(12) United States Patent
Masson et al.

(10) Patent No.: US 9,649,196 B2
(45) Date of Patent: *May 16, 2017

(54) SHOCK-ABSORBING SYSTEM FOR USE WITH A PROSTHETIC IMPLANT

(71) Applicant: Masson Development LLP, Houston, TX (US)

(72) Inventors: Marcos V. Masson, Houston, TX (US); Rafael R. Bernal, Houston, TX (US)

(73) Assignee: Masson Development LLP, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/954,424

(22) Filed: Nov. 30, 2015

(65) Prior Publication Data

US 2016/0151163 A1    Jun. 2, 2016

Related U.S. Application Data

(63) Continuation-in-part of application No. 14/873,820, filed on Oct. 2, 2015, now Pat. No. 9,554,913, and a continuation-in-part of application No. 14/082,855, filed on Nov. 18, 2013, now abandoned.

(51) Int. Cl.
*A61F 2/40* (2006.01)
*A61F 2/30* (2006.01)

(52) U.S. Cl.
CPC .... *A61F 2/4014* (2013.01); *A61F 2002/3055* (2013.01); *A61F 2002/30558* (2013.01); *A61F 2002/30561* (2013.01); *A61F 2002/30566* (2013.01); *A61F 2002/404* (2013.01); *A61F 2002/4022* (2013.01)

(58) Field of Classification Search
CPC ...... A61F 2/3609; A61F 2/367; A61F 2/4014; A61F 2/32; A61F 2/36; A61F 2/38; A61F 2/4059; A61F 2/4081; A61F 2002/30563; A61F 2002/30565; A61F 2002/30505; A61F 2002/30568

See application file for complete search history.

(56) References Cited

U.S. PATENT DOCUMENTS

| | | | |
|---|---|---|---|
| 5,080,673 A | 1/1992 | Burkhead et al. | |
| 5,201,881 A | 4/1993 | Evans | |
| 5,389,107 A | 2/1995 | Nassar et al. | |
| 6,336,941 B1 | 1/2002 | Subba Rao et al. | |
| 8,070,823 B2 | 12/2011 | Kellar et al. | |
| 8,591,591 B2 | 11/2013 | Winslow et al. | |
| 2002/0143402 A1 | 10/2002 | Steinberg | |
| 2004/0030400 A1* | 2/2004 | Horber | A61F 2/4014 623/22.43 |
| 2006/0064169 A1 | 3/2006 | Ferree | |
| 2012/0303130 A1* | 11/2012 | Winslow | A61F 2/4081 623/19.12 |

* cited by examiner

*Primary Examiner* — Brian Dukert
(74) *Attorney, Agent, or Firm* — Egbert Law Offices, PLLC (57) ABSTRACT

A shock-absorbing system for use in joint replacement arthroscopy has a bearing surface, a mounting base affixed to or formed with the bearing surface, a convex element extending outwardly of the mounting base opposite the bearing surface, a receptacle positioned so as to slidably or pivotably receive a portion of the convex element therein, a housing receiving at least a portion of the receptacle therein, and a resilient element received in the housing and bearing against a surface of the housing and against a surface of the receptacle.

16 Claims, 4 Drawing Sheets

SHOCK-ABSORBING SYSTEM FOR USE WITH A PROSTHETIC IMPLANT

CROSS-REFERENCE TO RELATED APPLICATIONS

The present application is a continuation-in-part of U.S. patent application Ser. No. 14/873,820, filed on Oct. 2, 2015, and entitled "Shock-Absorbing Implant for Use in Shoulder Arthroscopy", presently U.S. patent application Ser. No. 14/873,820 is a continuation-in-part of U.S. patent application Ser. No. 14/082,855, filed on Nov. 18, 2013 and entitled "Shock-Absorbing Humeral Implant for Shoulder Arthroscopy", presently U.S. application Ser. No. 14/082,855 claimed priority from U.S. Provisional Application Ser. No. 61/751,349, filed in Jan. 11, 2013 and entitled "Shock-Absorbing Implant with Pressure Adjustment and Sensing for Reverse Shoulder Arthroscopy". Additionally, U.S. patent application Ser. No. 14/082,855 claimed priority from U.S. Provisional Application Ser. No. 61/727,399, filed in Nov. 16, 2012 and entitled "Shock-Absorbing Implant for Use in Reverse Shoulder Arthroscopy".

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

INCORPORATION-BY-REFERENCE OF MATERIALS SUBMITTED ON A COMPACT DISC

Not applicable.

BACKGROUND OF THE INVENTION

1. Field of the Invention

The present invention relates to joint replacement surgery. More particularly, the present invention the relates to prosthetic implants that are used as joint replacement. More particularly, the present invention the relates to a modular shock-absorbing element incorporated into such implants so as to avoid the risk of fracture and damage to either the surrounding bone and/or implant.

2. Description of Related Art Including Information Disclosed Under 37 CFR 1.97 and 37 CFR 1.98

Joint replacement surgery is a procedure of orthopedic surgery in which an arthritic or dysfunctional joint surface is replaced with an orthopedic prosthesis. Joint placement is considered as a treatment when severe joint pain or dysfunction is not alleviated by less-invasive therapies. Joint replacement surgery is becoming more common with knees and hips replaced most often.

In recent decades, the most successful and common form of arthroplasty is the surgical replacement of a joint or joint surface with a prosthesis. For example, a hip joint that is affected by osteoarthritis may be replaced entirely with a prosthetic hip. The procedure involves replacing both the acetabulum and the head and neck of the femur. The purpose of doing the surgery as to relieve pain, to restore range of motion and to improve walking ability. This can lead to an improvement of muscle strength. Other forms of joint replacement surgery can include knee replacement, elbow replacement and shoulder replacement.

Every year, thousands of conventional total shoulder replacements are successfully carried out in the United States for patients with shoulder arthritis. This type of surgery, however, is not as beneficial for patients with large rotator cuff tears who have developed a complex type of shoulder arthritis called "cuff tear arthropathy". For these patients, conventional total shoulder replacement may result in pain and limited motion, and reverse total shoulder replacement may be an option.

A conventional shoulder replacement device mimics the normal anatomy of the shoulder. In other words, a plastic cup is fitted into the shoulder socket (glenoid), and a metal ball is attached to the top of the humerus. In a reverse total shoulder replacement, the socket and metal ball are switched. The metal ball is fixed to the socket and the plastic cup is fixed to the upper end of the humerus.

A reverse total shoulder replacement works better for people with cuff tear arthropathy because it relies on different muscles to move the arm. In a healthy shoulder, the rotator cuff muscles help position and power the arm during the range of motion. A conventional replacement device also uses the rotator cuff muscles to function properly. In a patient with a large rotator cuff tear and cuff tear arthropathy, these muscles are no longer functional. The reverse total shoulder replacement relies on the deltoid muscle, instead of the rotator cuff, to power and position the arm.

Subsequent to the shoulder replacement surgery, the implant can be subjected to a large variety of forces. In particular, if a patient should fall, the implant may be subjected to extremely large impact forces. These impact forces have been known to fracture the ball which is attached to the glenoid. In other circumstances, the scapula can become fractured because of an impact. In other circumstances, the connection between the socket and the humerus can become loosened or detached. In still other circumstances, the humeral shaft can become fractured as a result of these forces.

Whenever these forces cause a damage to either the implant or to the bone structure, additional surgery may be necessary. Since the ball is attached to the glenoid, it becomes quite difficult to repair and replace the ball after installation. As a result, the implant can become loosened or nonfunctional. In particular, in shoulder replacement surgery, repairs to the implant, following the surgery, are quite complex. As such, a need has developed so as to provide a shoulder implant structure which avoids the damage that can occur from sharp impact forces imparted to the implant.

Shock-absorbing structures have been known to be used in hip replacement surgery. In particular, a variety of patents have issued relating to such shock-absorbing structures. In particular, U.S. Pat. No. 5,201,881, issued on Apr. 13, 1993 to D. L. Evans, shows a joint prosthesis that provides articulating prosthesis components that can deflect with respect to one another so that shock absorption is provided. This serves to lower impact stresses. The components interface at articulating surfaces. A gap is provided at a position away from the articulating surfaces. As a result, one of the components can flex into the gap area during use.

U.S. Pat. No. 5,389,107, issued on Feb. 14, 1995 to Nassar et al., provides a shock absorbent prosthetic hip implant that includes a socket section that is attachable to the pelvic bone and a ball section that is pivotably engaged with the socket section. There is a first shock absorber section attached to the ball section and a second shock absorber section attached to an upper part of the femur bone. The second shock absorber section slidably engages the first shock absorber section. A spring is disposed between the first and second shock absorber sections for cushioning a compressive force applied between the femur and pelvic bones.

U.S. Pat. No. 6,336,941, issued on Jan. 8, 2002 to Subba Rao et al., discloses a modular hip implant with a shock absorption system. The shock absorption system absorbs compressive stresses that are imparted to the implant. A unique coupling member houses a modular spring mechanism that serves as the shock absorber.

U.S. Pat. No. 8,070,823, issued on Dec. 6, 2011 to Kellar et al., teaches a prosthetic ball-and-socket joint. This ball-and-socket joint includes first member having a balanced centroidal axis and includes a rigid material with a concave interior defining a cup surface. The cup surface includes a cantilevered first flange defining a wear-resistant protruding first contact rim. The first flange is asymmetric relative to the balanced centroidal axis. A cantilevered second flange defines a wear-resistant protruding second contact rim. The second member is made of a rigid material with a wear-resistant convex contact surface. The first and second contact rims bear against the contact surface of the second member to transfer loads between the first and second members while allowing pivoting motion therebetween. The flanges are shaped and sized to deform elastically and permit the first and second contact rims to conform in an irregular shape to the contact surface when the joint is under load.

U.S. Patent Publication No. 2002/0143402, published on Oct. 3, 2002 to A. Steinberg, shows a hip joint prostheses that has at least a first and a second load-carrying member. The first load-carrying member is substantially more shock absorbing and resilient than the second load-carrying member.

U.S. Patent Publication No. 2006/0064169, published on Mar. 23, 2006 to B. A. Ferree, discloses shock-absorbing joint and spine replacements. In particular, the joint is a total knee replacement. This total knee replacement implant includes a femoral component having a wheel. The implant has a tibial component that includes a shock-absorbing component with a piston assembly and spring. The implants contain a cushioning or shock-absorbing member to dampen axial loads and other forces. Fluid is forced rapidly from the device wherein compression and dampening is achieved by valves or other pathways that allow for a slower return of the fluid back into the implant as the pressure is relieved.

It is quite natural that shock-absorbing systems have been utilized for knee and hip replacements since the knee and the hip are often subjected to large impact forces. However, typically, with shoulder replacements, the shoulders are not subjected to such strong forces, unless the patient should fall or be involved in an accident. As such, in the past, shock-absorbing systems for shoulder replacement implants have not been developed. As a result, under those circumstances where a patient should fall or be involved in an accident, extensive surgery can be necessary so as to repair the implant and/or the surrounding bone structures. As such, a need has developed so as to provide a shock-absorbing implant for shoulder replacement surgery.

U.S. Pat. No. 6,336,941, issued on Jan. 8, 2002 to Subba Rao et al., shows a modular implant with a shock absorption system. This is a modular implant that can be custom fit to an individual patient. The shock absorption system absorbs compressive stresses that are imparted to the implant. The size of the femoral ball member, size of the femoral stem, femoral neck length, and tension in the shock absorber system is available for all individually adjustable parameters, depending on the particular patient. A coupling member houses a modular spring mechanism that serves as the shock absorber. The coupling member is received into the ball member to an adjustable depth, the adjustment of which varies the length of the femoral neck.

U.S. Pat. No. 8,591,591, issued on Nov. 26, 2013 to Winslow et al., discloses a spring base glenosphere. In particular, this is a reverse modular humeral implant for implantation into a humerus that includes a natural humeral shaft and a natural humeral head. The implant includes a humeral stem implantable into the natural humeral shaft, and an adapter couplable to the humeral stem. The adapter includes an anchoring projection configured to be coupled to a convex bearing.

U.S. Pat. No. 5,080,673, issued on Jan. 14, 1992 to Burkhead et al., describes a glenoid prosthesis and method of use. The glenoid prosthesis has a lateral surface for articulating with the humeral head and a flat medial surface which engages a flat surface resected from the glenoid cavity. A pair of pegs extend medially from the flat medial surface of the glenoid prosthesis which are positioned in a pair of holes and the mating flat surfaces and pegs and holes are bonded with cement.

It is quite natural that shock-absorbing systems have been utilized for knee and hip replacements since the knee and the hip are often subjected to large impact forces. However, typically, with shoulder replacements, the shoulder prostheses are not subjected to such strong forces, unless the patient should fall or be involved in an accident. In the past, shock-absorbing systems for shoulder replacement implants have not been developed. As a result, under those circumstances where a patient should fall or be involved in an accident, extensive surgery can be necessary so as to repair the implant and/or the surrounding bone structures. As such, a need has developed so as to provide a shock-absorbing implant for shoulder replacement surgery.

It is an object of the present invention to provide a shock-absorbing portion of an implant which redistributes forces in a controlled and expected manner, thus limiting the excessive motion from a sudden blow or impact.

It is another object of the present invention to provide a shock-absorbing portion of an implant which mitigates micro-motion.

It is another object of the present invention to provide a shock-absorbing portion of an implant which creates a weak link such that an easily repairable portion of the implant will fail prior to a less easily repaired component of the implant.

It is still a further object of the present invention provide a shock-absorbing portion of an implant which avoids any fracturing of the bone and/or damage to the implant.

It is another object of the present invention to provide a shock-absorbing portion of an implant which is easily replaceable.

It is another object of the present invention to provide a shock-absorbing portion of an implant which provides a low-friction coupling between the elements of the implant.

It is still another object of the present invention to provide a shock-absorbing portion of an implant which allows the implant to return to its original configuration upon absorbing or receiving an impact.

It is yet another object of the present invention to provide a shock-absorbing portion of an implant which is modular and can be used with implants for a variety of joints.

These and other objects and advantages of the present invention will become apparent from a reading of the attached specification and appended claims.

BRIEF SUMMARY OF THE INVENTION

The present invention is a shock-absorbing portion of a prosthetic implant for use in joint replacement surgery. This shock-absorbing portion comprises a bearing surface, a mounting base affixed to or formed with the bearing surface, a convex element extending outwardly of the mounting base opposite the bearing surface, a receptacle positioned so as to slidably or pivotably receive a portion of the convex element therein, a housing receiving at least a portion of the receptacle therein, and a resilient element received in the housing and bearing against a surface of the housing and against a surface of the receptacle.

In the present invention, the bearing surface has a concavity formed on a surface thereof opposite the mounting base. A beam ring is interposed between the convex element and the receptacle. This beam ring is preferably circular, but can actually be of any geometric configuration. The beam ring extends radially outwardly of the convex element. The beam ring includes a central ring and a plurality of arms extending radially outwardly of the central ring. The plurality of arms bear against a side of the mounting base opposite the bearing surface. The central ring has an opening in an interior thereof. The convex element extends through this opening. Importantly, the configuration, size and shape of the central ring and the arm can be modified so as to custom fit to the needs of the patient.

The receptacle has a first portion and a second portion. The first portion has a concavity formed therein. This concavity receives a portion of the convex element therein. This portion of the convex element has a convexity with a radius that is less than a radius of the concavity of the first portion of the receptacle.

The housing has a well formed therein. The well has a first portion and a second portion. In one embodiment, the first portion has an inner diameter greater than an inner diameter of the second portion. The resilient element bears against the first portion of the receptacle. The previously-described surface of the housing is a shoulder formed at the bottom of the first portion of the well of the housing. The second portion of the receptacle is received in the second portion of the housing. Alternatively, the resilient member is received in the second portion of the housing and bears against the first portion of the receptacle. The housing includes a first housing element and a second housing element affixed to the first housing element. The second housing element retains the receptacle within the first housing element. The convex element extends through a wall of the second housing element so as to fit against the concave surface of the receptacle. The housing can be part of an implanted stem or a modular item that attaches to it or the implant anchor itself. The present invention thereby lends itself to customization.

The convex element of the present invention includes a partially spherical element and a stem extending outwardly of the partially spherical element. The stem has an end opposite the partially spherical element that is affixed to the mounting base. The convex element has a junction portion between the partially spherical element and the stem. In one embodiment, the junction portion has a diameter less than a maximum of diameter of either of the partially spherical element and the stem.

In the present invention, a plurality of fasteners are affixed to the mounting base to the beam ring. Also, in the present invention, the resilient element is a spring. In those circumstances when the shock-absorbing element is a glenoid implant, then the bearing surface is concave. In those cases where the shock-absorbing system is for a humeral head, the bearing surface is convex.

This foregoing section is intended to describe, with particularity, the preferred embodiments of the present invention. It is understood that modifications to these preferred embodiments can be made within the scope of the present invention. As such, this section is not construed, in any way, as limiting of the broad scope of the present invention. The present invention should only be limited by the following claims and their legal equivalents.

DETAILED DESCRIPTION OF THE INVENTION

Figure 1:
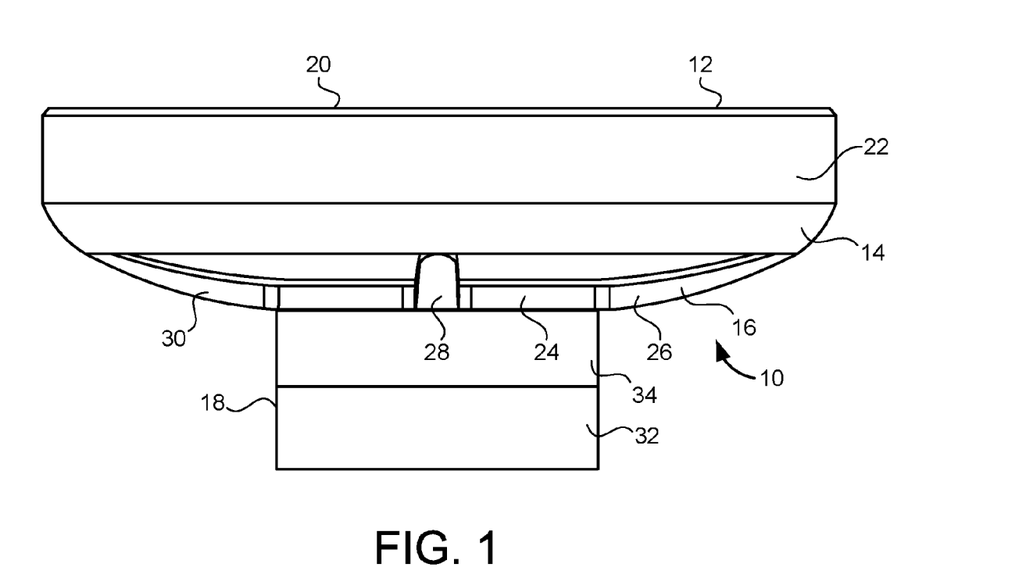
FIG. 1 is a side elevational view of the shock-absorbing system in accordance with the preferred embodiment of the present invention.

Referring to FIG. 1, there is shown the shock-absorbing system of a prosthetic implant in accordance with the preferred embodiment of the present invention. In particular, the shock-absorbing system 10 is illustrated as a glenoid implant. However, the structure of the present invention is modular and can be easily adapted for use in a variety of other joint replacements. The shock-absorbing system 10 includes a bearing surface 12, a mounting base 14 affixed to or formed with the bearing surface 12, a beam ring 16 secured to the underside of the mounting base 14 opposite the bearing surface 12, and a housing 18 positioned below the beam ring 16. As will be described hereinafter, the mounting base 14 will support a convex element such that the convex element extends downwardly. The receptacle is positioned within the housing 18 so as to slidably or pivotally receive a portion of the convex element thereon.

In FIG. 1, the bearing surface 12 can have an outer surface 20 that serves to bear against an opposing element of the joint replacement, such as a humeral head or humeral head implant. The outer surface 12 can be of a variety of materials. In particular, certain ceramic materials can be used such as alumina, zirconia silica, hydroxyapatite, titanium nitride or silicon nitride. A combination of titanium and titanium carbide is a very hard ceramic material often used as components of arthroplasties due to the impressive degree of strength and toughness. It also presents compatibility with medical imaging. In other circumstances, the outer surface can be of a polymeric or elastomeric material, such as TEFLON™. As such, the humeral head or the humeral head implant can bear against the surface 20 in a natural and conventional manner. The bearing surface 12 has a side 22 extending outwardly of the surface 20. As such, the side 22 provides support for the surface 20. The mounting base 14 is affixed to the bearing surface 12 at the side opposite to surface 20. As such, the mounting base 14 can provide strong structural support for the bearing surface 12. The beam ring 16 includes a central ring 24 with a plurality of arms 26, 28 and 30 radiating outwardly therefrom. As such, the central ring 24 will be interposed between the housing 18 and the mounting base 14. The arms 26, 28 and 30 radiate outwardly so as to provide support for the outer periphery of the mounting base 14 and the attached bearing surface 12. The housing 14 includes a first housing element 32 and a second housing element 34. These housing elements 32 and 34 are fitted together, adhesively secured together, in a snap-fit relationship, or screwed together, so as to enclose the receptacle and the convex element therein as will be described hereinafter.

Figure 2:
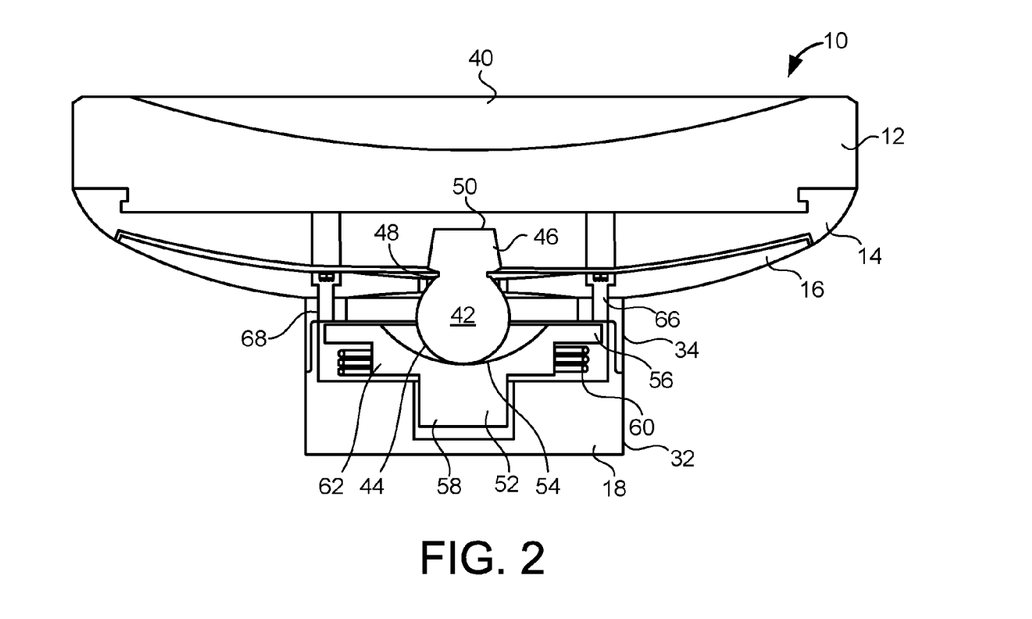
FIG. 2 is a cross-sectional view of the shock-absorbing system of the preferred embodiment the present invention.

FIG. 2 shows a cross-sectional view of the shock-absorbing system 10. In particular, it can be seen that the bearing surface 12 includes a concavity 40 therein. As stated hereinbefore, this concavity will conform to the shape of the opposite element of the implant, such as the humeral head or to the humeral head implant. The mounting base 14 is secured to the side of the bearing surface 12 opposite the concavity 40. It can be seen that there is a convex element 42 that includes a partially spherical element 44 and a stem 46. There is a junction 48 between this partially spherical surface 44 and the stem 46. The junction 48 has a diameter that is less than the maximum diameter of either the stem 46 or the partially spherical element 44. The stem 46 of the convex element 42 is affixed within a receptacle 50 formed into the mounting base 14. As a result, the convex element 42 will extend outwardly from the mounting base 14 opposite to the bearing surface 12.

A receptacle 52 is provided so as to have a concave surface 54 thereon. As can be seen, the partially spherical element 44 of convex element 42 resides within the concavity 54. Concavity 54 allows the convex element 42 to pivot therein and/or to slidably move therein.

The receptacle 52 includes a first portion 56 and a second portion 58. The second portion 58 extends from the first portion 56 in a direction away from the convex element 42. A resilient member 60 is positioned within the housing 18 so as to bear against the first portion 56. The resilient element 60 is in the nature of a spring that can wrap around an annular portion 62 of the receptacle 52. The resilient element 60 will urge the receptacle 52 in a direction toward the convex element 42 such that the partially spherical element 44 of convex element 42 will bear against the surface of the concavity 54.

In FIG. 2, the housing 18 includes a first portion 32 and a second portion 34. The second portion 34 is fitted over the first portion 32 so as to enclose the receptacle 52 within the first portion of housing 18. Suitable fasteners 66 and 68 can be used so as to secure the beam ring 16 to the mounting base 14.

Figure 3:
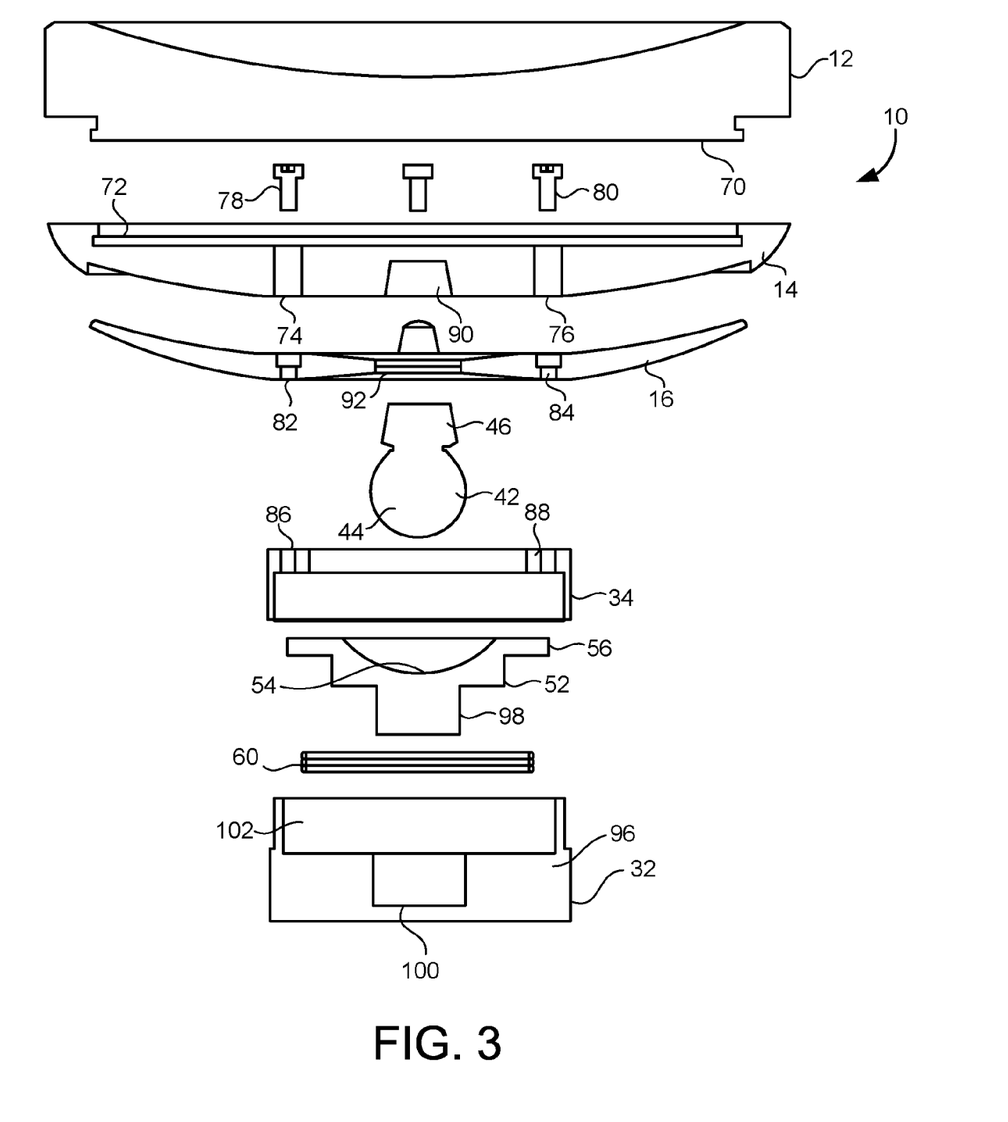
FIG. 3 is an exploded view of the shock-absorbing system of the present invention.

FIG. 3 is an exploded view of the shock-absorbing implant of the present invention. In particular, FIG. 3 shows the bearing surface 12, the mounting base 14, the beam ring 16, the convex element 42, the receptacle 52, the first housing element 32, the second housing element 34, and the resilient element 60.

The bearing surface 12 includes a protrusion 70 that is adapted to be snap-fit within a receptacle 72 formed on the adjacent surface of the mounting base 14. Alternatively, and within the concept of the present invention, the mounting base 14 can be directly formed with or integrally attached to the bearing surface 12. As such, the bearing surface 12 is securely fixed to the mounting base 14.

The mounting base 14 includes holes 74 and 76 therethrough. Holes 74 and 76 are configured so as to allow respective fasteners 78 and 80 to extend through the holes 74 and 76 so as to be fitted within the respective holes 82 and 84 of the beam ring 16. Additionally, the ends of the fastener 78 and 80 can threadedly engaged with holes 86 and 88 of the second housing element 34. In this manner, the beam ring 16 can be securely sandwiched between the mounting base 14 and the second housing element 34.

FIG. 3 shows that there is an opening 90 formed on a side of the mounting base 14 opposite the bearing surface 12. This opening 90 will serve to receive the stem 46 of the convex element 42. The stem 46 can extend through an opening 92 in the beam ring 16 such so as to fix the position of the convex element 42 therein. The junction portion of the convex element 42 can be in snap-fit relationship with the sides of the opening 92 of beam ring 16.

The partially spherical element 44 of the convex element 42 will extend through a hole formed in the top surface of the second housing element 34 so as to extend downwardly and fit within the concavity 54 of the receptacle 52. The resilient element 60 is adapted so as to bear against the surface 56 of the receptacle 52 and against a surface 96 of the first housing element 32. The receptacle 52 also includes a second portion 98 that is adapted to be received within a second portion 100 of a well 102 formed in the interior of the first housing element 32. As such, the second portion 98 of the receptacle 52 can securely nest within the well 102 of the housing 18. In this manner, the resilient element 60 can resiliently bear against the receptacle 52 in a secure manner.

Figure 4:
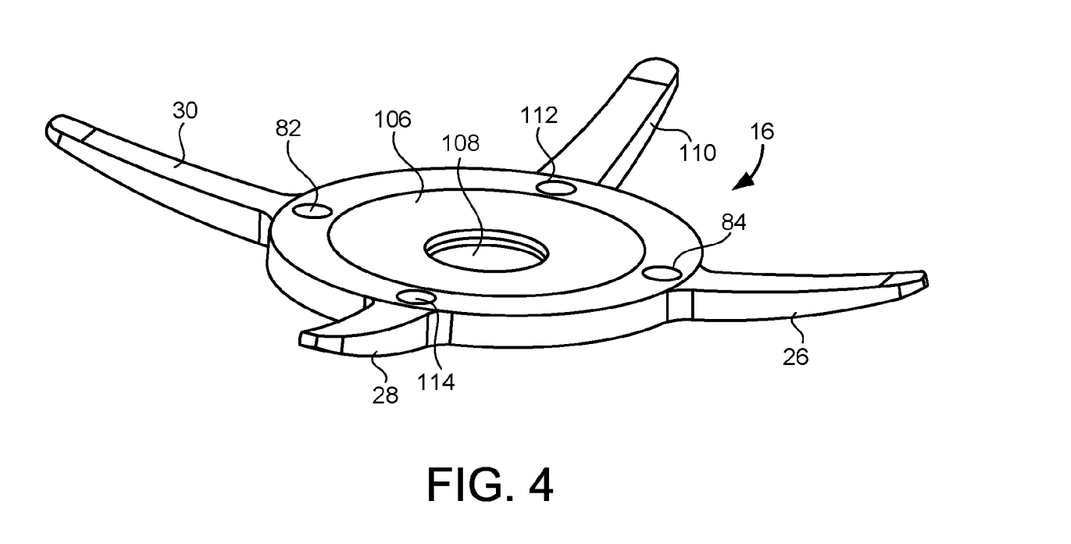
FIG. 4 is an upper perspective view showing the beam ring as used in the shock absorbing system of the present invention.

FIG. 4 is an isolated view of the beam ring 16. The beam ring 16 includes a central ring 106 having a hole 108 formed centrally thereof. The central ring 106 is illustrated as having a circular shape. However, the central ring 106 can also have a variety of other geometric configurations. A plurality of arms 26, 28, 30 and 110 radiate outwardly in circumferentially spaced relationship from the central ring 106. Bolt holes 82, 84, 112 and 114 are formed through the thickness of the central ring 106.

Importantly, in FIG. 4, it can be seen that each of the arms 26, 28, 30 and 110 has a width that decreases from the central ring 106 to an opposite end of each of the arms. Similarly, each of the arms 26, 28, 30 and 110 has a thickness that decreases from the central ring 106 to the outer end of each of the arms. As such, each of the arms is configured to have greater flexibility at the periphery of the beam ring 16 than adjacent to the central portion of the beam ring.

Importantly, the present invention offers unique advantages as a shock-absorbing implant. In particular, a rotation of the convex element 42 with respect to the concavity 54 is allowed. Additionally, since the concavity 54 has a radius that is greater than the radius of the convexity of the convex element 42, a gliding effect is also allowed, along with a small translation relative to these elements. Additionally, the beam ring 16 can act as a spring so as to absorb impact forces while allowing the beam ring, and the associated structures, to return to their original configuration. The cross-section reduction (width and thickness) described herein is a preferred embodiment. The moment and inertia of each and every beam can be adapted to the needs of the patient so as to allow it to be custom-fit.

If any impact were to occur to the surface 20 of the bearing surface 12, the shock-absorbing system 10 of the present invention is able to diffuse such an impact by having small displacements on several elements. In particular, the arms 26, 28, 30 and 110 of the beam ring 16 will flex individually and/or at the same time. The gliding joint mechanism provided between the convex element 42 and the concavity 54 of receptacle 52 will redirect the impact toward a single degree of freedom (i.e. translation along a single axis). Additionally, and furthermore, the resilient element 60 (i.e. a spring) will collect the impact energy and restore the system to the original position afterward.

If a shearing action is applied to the implant 10, then the present invention includes built-in security in order to secure the preservation of the bone to which the implant is attached. In particular, the gliding joint mechanism provided between the convex element 42 and the concavity 54 of receptacle 52 has a reduced cross-sectional area at the element connecting the base plate to the mechanism. This reduction of areas intended to break under shear. This maximizes the potential for bone preservation. Additionally, each or any of the beams 26, 28, 30 and 110 could also bend or break in order to avoid damage to the connected bone. In the event that any of the elements associated with the implant 10 were to fail, the replacement would not compromise the bone that is used to fixate the system.

It should be noted that the clearance provided between the bottom of the surface 56 of receptacle 52 and the shoulder 96 of the housing 18 allows for a single axis translational motion of the spring. This clearance could be filled with an elastomer, a silicone, or similar materials, in order to enhance the shock-absorption capabilities of the system. This clearance could also be used so as to allow for a fluid to fill it so as to provide a natural damper. The filling liquid could be blood, synovial fluid, or a combination of both.

In the embodiment shown in FIGS. 1-3, the shock-absorbing system 10 is intended for use as a joint replacement prosthesis. In order to properly secure the implant, the housing 18 can be properly secured by nails or screws within the bone tissue provided at one side of the joint. As such, the surface 20 of the bearing surface 12 can face outwardly in the direction toward the other side of the joint. The fixation mechanisms (i.e. nails or screws) may also be constructed of materials that degrade under specific temperature, chemical or structural ranges of conditions. Within the concept of the present invention, the components of the shock-absorbing system 10 can be reversed, as required. As such, the housing 18 could be properly secured by nails or screws within the bone tissue provided at the other side of the joint while the surface 20 of the bearing surface can face outwardly in the direction of the side of the joint. It is not critical within the concept of the present invention as to which of the component is placed on one portion of the joint and the other component placed on the other portion of the joint. The shock-absorbing implant of the present invention is completely reversible.

Figure 5:
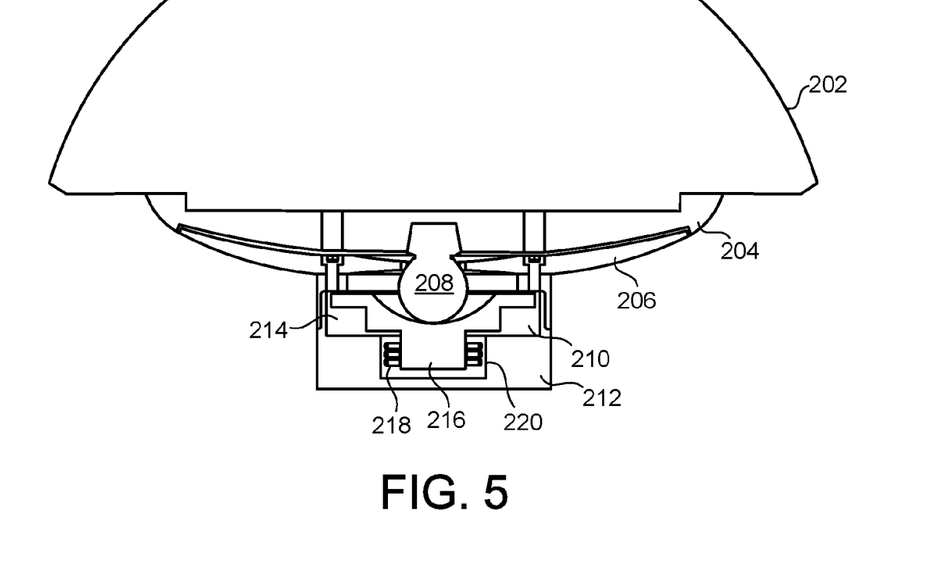
FIG. 5 is a cross-sectional view of an alternative embodiment of the shock-absorbing system of the present invention.

In FIG. 5, there shown the shock-absorbing system 200 in accordance with the teachings of the present invention. Shock-absorbing system 200 has a configuration similar to that shown in the previous embodiment except for the fact that the bearing surface 12 is actually a convex surface 202. Convex surface 202 will mimic the surface of the humeral head. As such, there is a smooth contoured surface 202 that can bear against the cup of the joint or the cup of the other element of the implant. A mounting base 204 is secured to the convex bearing surface 202 in the manner described herein previously. A beam ring 206 is affixed to the surface of the mounting base 204 opposite the convex bearing surface 202. The convex element 208 is secured so as to extend to a receptacle 210. Receptacle 210 is received within a housing 212.

Unlike the previous embodiment of the present invention, it can be seen that the receptacle 210 includes a first portion 214 and a second portion 216. The resilient element 218 is received in the well 220 of the housing 212 so as to extend around the second portion 216 and to bear against the first portion 214. In contrast to the previous embodiment, it can be seen that the spring 218 is received within the smaller inner diameter portion of the well 220 rather than in the larger inner diameter portion of the well. Within the concept of the shock-absorbing system 200, as shown in FIG. 5, it is also possible that the configuration of spring and surfaces of the receptacle could be similar to that shown in the previous embodiment.

Figure 6:
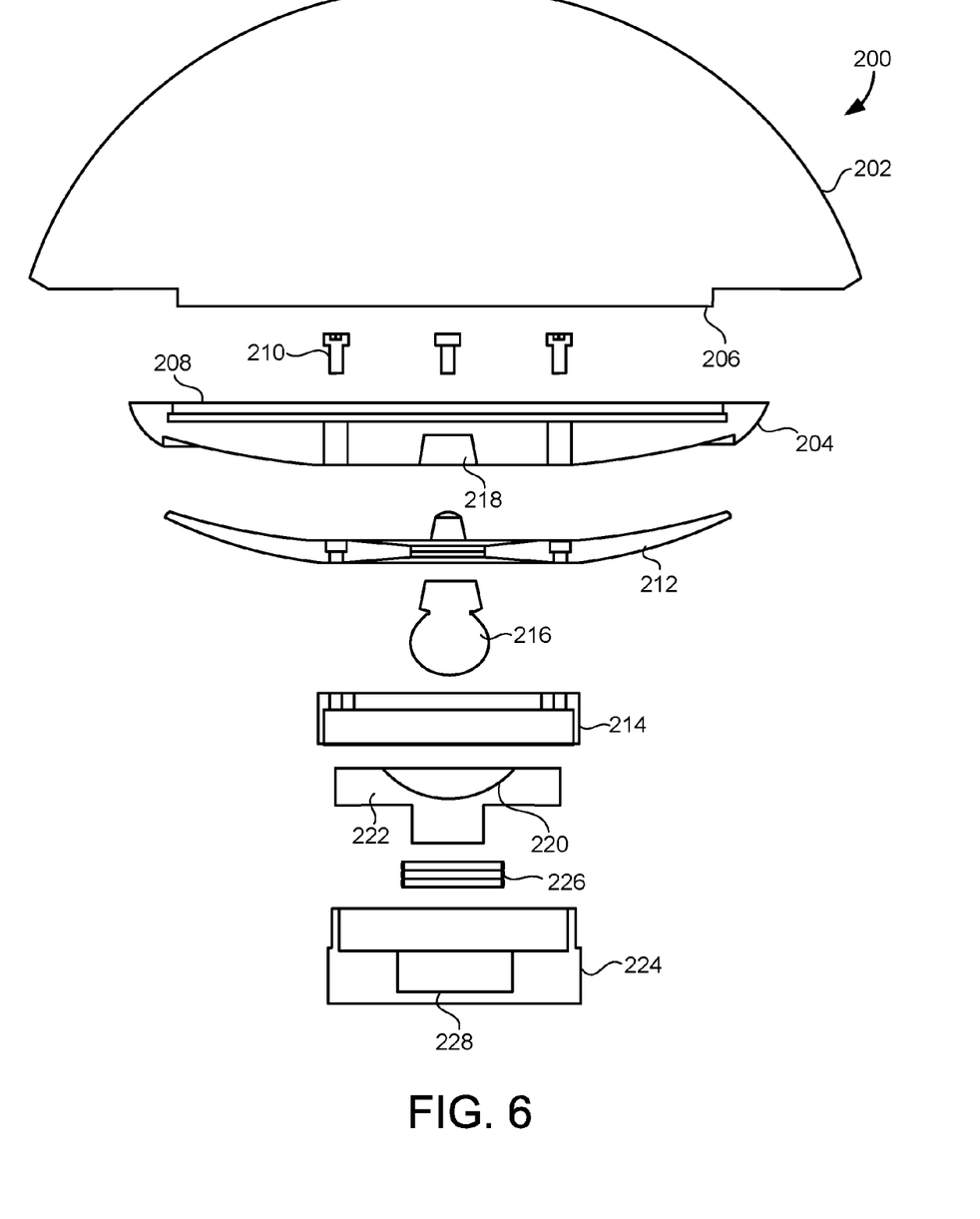
FIG. 6 is an exploded view of the alternative embodiment of the shock-absorbing system of the present invention.

FIG. 6 illustrates an exploded view of the shock-absorbing head system 200 in accordance with this alternative embodiment of the present invention. In particular, it can be seen that the convex bearing surface 202 can be affixed to the mounting plate 204 by virtue of the protrusion 206 that is received within the receptacle 208 formed on the mounting base 204. Fasteners 210 extend through the mounting base 204 and through holes in the beam ring 212 so as to engage with the second housing element 214. The convex element 216 is affixed within the opening 218 of the mounting base 204, extends through the beam ring 212, and has a convex surface bearing against a concavity 220 of the receptacle 222. The first housing element 224 receives the spring 226 within a lower well 228 such that the spring 226 can bear against the shoulder of the receptacle 222. The second housing element 214 can be fitted over the male end of the first housing element 224 so as to enclose the receptacle 220 and the spring 226 therein.

In the embodiments of FIGS. 5 and 6, the housing 220 can be affixed, in a conventional fashion, to the bone structure available at the joint, such as the humeral head. As such, the convex bearing surface 202 can extend outwardly at a conventional angle toward the other side of the joint, such as the glenoid. The head implant system 200 can be used in conjunction with an existing cup structure, such as the glenoid, or with the shock-absorbing system 10 of FIGS. 1-3.

Within the present invention, is important to note that the bearing surface of the shock-absorbing implant can be easily exchanged. If it is desired to be used in a glenoid implant, then the bearing surface 12 of FIGS. 1-3 can be used. Alternatively, if the shock-absorbing system is intended as part of a humeral head implant, then the convex bearing surface 202 of FIGS. 5 and 6 can be utilized. As such, it is easy to adapt the shock-absorbing system for different purposes, such as knee replacements, hip replacement, or elbow replacements. The present invention can also be used as part of a regular shoulder joint replacement or as part of a reverse shoulder joint replacement. The entire shock-absorbing system is intended to be positioned as near as possible to the joint. However, it should not be limited to this since it can be actuated by other methods as well.

The foregoing disclosure and description of the invention is illustrative and explanatory thereof. Various changes in the details of the illustrated construction can be made within the scope of the present claims without departing from the true spirit of the invention. The present invention should only be limited by the following claims and their legal equivalents.

We claim:

1. A shock-absorbing system for use in joint replacement arthroplasty, the shock-absorbing system comprising:
   a bearing surface;

a mounting base affixed to or formed with said bearing surface;

a convex element extending outwardly of said mounting base opposite said bearing surface;

a receptacle positioned so as to slidably or pivotably receive a portion of said convex element therein;

a housing receiving at least a portion of said receptacle therein, said housing having a surface thereon;

a resilient element received in said housing and bearing against said surface of said housing and against a surface of said receptacle; and a beam ring interposed between said convex element in said receptacle, said beam ring extending radially outwardly of said convex element.

2. The shock-absorbing system of claim 1, said bearing surface having a concavity formed on a surface thereof opposite said mounting base.

3. The shock-absorbing system of claim 1, said bearing surface having a convexity formed on or attached to a surface thereof that is opposite said mounting base.

4. The shock-absorbing system of claim 1, said beam ring comprising:

a central ring of any geometric configuration; and a plurality of arms extending radially outwardly of said central ring, said plurality of arms bearing against a side of said mounting base opposite said bearing surface.

5. The shock-absorbing system of claim 4, each of said plurality of arms reducing in width from said central ring toward an outer end of the arm.

6. The shock-absorbing system of claim 4, each of said plurality of arms reducing in thickness from said central ring toward an outer end of the arm.

7. The shock-absorbing system of claim 4, said central ring having an opening in an interior thereof, said convex element extending through said opening.

8. A shock-absorbing system for use in joint replacement arthroplasty, the shock-absorbing system comprising:

a bearing surface;

a mounting base affixed to or formed with said bearing surface;

a convex element extending outwardly of said mounting base opposite said bearing surface;

a receptacle positioned so as to slidably or pivotably receive a portion of said convex element therein;

a housing receiving at least a portion of said receptacle therein, said housing having a surface thereon;

a resilient element received in said housing and bearing against said surface of said housing and against a surface of said receptacle, said receptacle having a first portion and a second portion, said first portion having a concavity formed therein, said concavity receiving the portion of said convex element therein, said portion of said convex element having a convexity having a radius, said concavity of said first portion of said receptacle having a radius, the radius of said concavity being greater than the radius of said convexity.

9. The shock-absorbing system of claim 8, said housing having a well formed therein, said well having a first portion and a second portion, said first portion having an inner diameter greater than an inner diameter of said second portion, said resilient element bearing against said first portion of said receptacle, said surface of said housing being a shoulder formed at a bottom of said first portion of said well of said housing.

10. The shock-absorbing system of claim 9, said second portion of said receptacle received in said second portion of said housing.

11. The shock-absorbing system of claim 8, said housing having a well formed therein, said well having a first portion of a second portion, said first portion having an inner diameter greater than an inner diameter of said second portion, said resilient element received in said second portion of said housing and bearing against said first portion of said receptacle.

12. A shock-absorbing system for use in joint replacement arthroplasty, the shock-absorbing system comprising:

a bearing surface;

a mounting base affixed to or formed with said bearing surface;

a convex element extending outwardly of said mounting base opposite said bearing surface;

a receptacle positioned so as to slidably or pivotably receive a portion of said convex element therein;

a housing receiving at least a portion of said receptacle therein, said housing having a surface thereon;

a resilient element received in said housing and bearing against said surface of said housing and against a surface of said receptacle, said housing comprising:

a first housing element; and a second housing element affixed to said first housing element, said second housing element retaining said receptacle within said first housing element, said convex element extending through a wall of said second housing element so as to fit against a concave surface of said receptacle.

13. The shock-absorbing system of claim 1, said convex element comprising:

a partially spherical element; and a stem extending outwardly of said partially spherical element, said stem having an end opposite said partially spherical element that is affixed to said mounting base.

14. The shock-absorbing implant of claim 13, said convex element having a junction portion between said partially spherical element and said stem, said junction portion having a diameter less than a maximum diameter of either of said partially spherical element and said stem.

15. The shock-absorbing system of claim 1, further comprising:

a plurality of fasteners affixing said mounting base to said beam ring.

16. The shock-absorbing system of claim 1, said resilient element being a spring.

* * * * *